United States Patent
Premo et al.

(10) Patent No.: US 8,603,443 B1
(45) Date of Patent: Dec. 10, 2013

(54) HIGH PHOTOSTABILITY SUNSCREEN COMPOSITION

(75) Inventors: Paul S. Premo, Beverly Hills, CA (US); Susan Goldsberry, Huntington Beach, CA (US); Mehrdad Jahedshoar, Newport Beach, CA (US)

(73) Assignee: CellCeuticals Skin Care, Inc., Beverly Hills, CA (US)

( * ) Notice: Subject to any disclaimer, the term of this patent is extended or adjusted under 35 U.S.C. 154(b) by 57 days.

(21) Appl. No.: 13/103,393

(22) Filed: May 9, 2011

Related U.S. Application Data

(60) Provisional application No. 61/332,265, filed on May 7, 2010.

(51) Int. Cl.
*A61K 8/49* (2006.01)
*A61K 8/37* (2006.01)
*A61Q 17/04* (2006.01)

(52) U.S. Cl.
USPC .................. 424/60; 424/59; 252/380; 512/2

(58) Field of Classification Search
USPC ............................ 424/60, 59; 252/380; 512/2
See application file for complete search history.

(56) References Cited

U.S. PATENT DOCUMENTS

2005/0025727 A1* 2/2005 Lott ................................ 424/59
2009/0068130 A1* 3/2009 Spaulding et al. .............. 424/60

OTHER PUBLICATIONS

Astaplacton HA: retrieved from internet: www.gelyma.com. Retrieved on Nov. 27, 2012.*
DSM Press Release: retrieved from internet: http://www.dsm.com/en_US/html/dnp/news_rel_2004_08.htm. Retrieved on Nov. 28, 2012.*
Dimethicodiethylbenzalmalonate: retrieved from internet: http://ec.europa.eu/consumers/cosmetics/cosing/index.cfm?fuseaction=search.details&id=28831. Retrieved on Nov. 27, 2012.*

* cited by examiner

*Primary Examiner* — Ernst Arnold
*Assistant Examiner* — Hong Yu
(74) *Attorney, Agent, or Firm* — Louis C. Paul

(57) ABSTRACT

A highly photostable, broad spectrum (UVA/UVB) sunscreen composition having an SPF of greater than 50 that retains about 90% of its UV absorbance over the range of 290 nm to 400 nm after being irradiated with 15 MEDs of energy from a simulated solar radiation source calibrated in accordance with the COLIPA standard. The highly photostable sunscreen composition is comprised of at least one dibenzoylmethane derivative, preferably avobenzone, and at least four compounds that quench singlet-excited energy and/or triplet excited energy, respectively "singlet quenchers" and "triplet quenchers".

7 Claims, No Drawings

HIGH PHOTOSTABILITY SUNSCREEN COMPOSITION

CROSS REFERENCE TO RELATED APPLICATIONS

This application claims the priority benefit of U.S. Provisional Application Ser. No. 61/332,265 filed on May 7, 2010, the contents of which are incorporated herein by reference in their entirety.

STATEMENT REGARDING FEDERALLY SPONSORED RESEARCH OR DEVELOPMENT

Not applicable.

FIELD OF THE INVENTION

The present invention is directed to topical compositions that provide protection from ultraviolet radiation ("UVR").

BACKGROUND OF THE INVENTION

The medical community, companies involved in the development and formulation of photoprotective consumer products, the popular press, and regulators have recognized the long term health consequences of exposure to ultraviolet radiation. It is well known that exposure to UVB light (290 nm-320 nm) causes erythema and sunburn. Longer term, exposure to short and long wavelength UVA rays (from about 320 nm to 400 nm) has been linked not only to photodamage—manifested as fines lines, rhtyids, lentigines, uneven pigmentation—but also actinic keratoses, impaired immune function and skin cancers.

Organic sunscreen filters prevent erythema and photodamage by absorbing a certain percentage of UVR over a specified spectrum. Sun protection factor ("SPF") is an expression of this percentage and theoretically indicates that the user is protected X times longer than without sunscreen. An SPF 33 product would, theoretically, allow 3% of unattenuated sunlight to reach the skin. Such a product would absorb 97% of erythemal UVR, allowing the user to conclude that he or she could stay out in the sun 33 times longer than without the sunscreen without erythema.

More recently, there has been increased focus on the contribution of UVA to these adverse health effects. This increased awareness of the importance of UVA protection resulted in the introduction of broad-spectrum sunscreens (having protection across the ultraviolet radiation spectrum, from 290 nm to 400 nm) and in FDA's Proposed Amendment of Final Sunscreen Monograph published in the Federal Register in Vol. 72, No. 165 at pages 49070 to 49122.

FDA is now proposing that both in vitro and in vivo tests be conducted to determine UVA radiation protection. The proposed in vitro test is the ratio of long wavelength UVA-1 absorbance (340 nm-400 nm) to total UV absorbance (i.e., UVB+UVA). The proposed in vivo test relates to persistent pigment darkening (PPD) test, which is similar to the SPF test except the endpoint is pigment darkening rather than erythema. FDA is proposing that UVA labeling consist of a UVA rating reflecting both the in vitro and in vivo test results, with sunscreen formulations that offer the highest UVA protection receiving a maximum of four stars.

Achieving broad-spectrum protection across the ultraviolet radiation spectrum (from 290 nm to 400 nm) requires sunscreen active ingredients that absorb, block or otherwise attenuate longer UVA-1 radiation. Avobenzone, zinc oxide and titanium dioxide are three sunscreen actives currently approved by the FDA that provide protection from longer UV wavelengths. (The recently approved Mexoryl SX sunscreen is effective against shorter wavelengths, having a maximum absorption at 344 nm.)

It is well-known in the art, however, that avobenzone rapidly undergoes photochemical degradation and is, therefore, not considered to be "photostable". Thus, the labeled SPF of a sunscreen formulation containing avobenzone is not necessarily reflective of the product's UVR protection.

Exposure to UVR dissipates the available concentration of the organic UV filters in a sunscreen formulation, resulting in a product with decreased efficacy, both in terms of level of protection and time of protection. In terms of photophysics, UVR exposure causes organic UV absorbing molecules to leave the ground state and enter the single-excited state. The excited-state filters may be returned to the ground state by singlet quenching (and thereby conserved to continue providing UVR protection), or transferred from the singlet-state to the triplet-excited state. In the triplet state, the UV filter molecule may undergo triplet quenching (and return to the ground state). If, however, triplet quenching (or another photophysical pathway) does not restore the sunscreen molecule to the ground state, the filter undergoes photodegradation by one or more photochemical reactions. Photodegraded filters lose their ability to filter UVR, thereby decreasing the effectiveness of the overall formulation.

In part recognizing the limitations of SPF, other metrics for sunscreen efficiency have been developed. Among these is photostability. In published articles and meetings of national and international Societies of Cosmetic Chemists, researchers have commented that broad-spectrum protection must remain efficient throughout the period of UVR exposure.

As used in the present application, the photostability of a UV filter can be measured and expressed in terms of the amount (i.e., concentration) by which the filter is degraded by one or more photochemical reactions, including photofragmentation, isomerization, tautomerization, photoaddition and substitution reactions, and/or cycloadditions. These photodegradation reactions also generate free radicals, which are associated with adverse health consequences.

Previous attempts to create photostable sunscreen formulations containing avobenzone are described in U.S. Pat. Nos. 7,235,587; 7,244,416; 6,444,195; 6,033,649; 6,071,501; 5,985,251; 5,849,273; 5,576,354; and 5,587,150. (To the extent pertinent, all published US patent application and granted US patents cited in the present application are incorporated by reference in their entirety.)

U.S. Pat. No. 5,776,439 teaches a photostable composition comprising from 1% to 10% avobenzone and from 0.5% to 10% oxybenzone, a UVB absorber. (Unless otherwise stated, percentages are weight/weight.)

Oxybenzone has a triplet excited state energy greater than 65 kcal/mol. The triplet excited state energy of avobenzone is less than 60 kcal/mol. At the September 2007 Annual Sunscreen Symposium organized by the Florida Chapter of the Society of Cosmetic Chemists, Bonda described several photophysical pathways for quenching singlet excited energy, including fluorescence. (Fluorescence is the emission of photons from the singlet excited.) Bonda reported that oxybenzone quenches avobenzone fluorescence and proposed a mechanistic explanation for the increased photostability of avobenzone in formulations containing oxybenzone. According to Bonda, oxybenzone likely reduces the flow of singlet excited state energy to the triplet-excited state, and thereby decreases the potential for photodegradative chemical reactions involving avobenzone.

Published U.S. Patent Application No. 2005/0013781 teaches a sunscreen composition comprising homosalate, octyl salicylate, oxybenzone, octocrylene and avobenzone.

There remains a need for a broad-spectrum sunscreen formulation having a high UVA rating of PFA +++ that exhibits a high degree of photostability and further comprises an effective antioxidant system to quench free radicals generated by photodegradation of sunscreen filters. This need is met by the composition of the present invention.

DETAILED DESCRIPTION OF THE INVENTION

The present invention is directed to sunscreen compositions consisting essentially of at least one dibenzoylmethane derivative, preferably avobenzone, and at least four compounds that quench singlet-excited energy and/or triplet-excited energy, respectively "singlet quenchers" and "triplet quenchers" TQ and collectively excited energy quenchers ("EEQs"). Commercial embodiments of the photostable sunscreen of the present invention can also include further ingredients such as emollients, surfactants, and carrier fluids, with the proviso that such further ingredients do not adversely affect the photostability of the sunscreen composition as measured by the method described herein. The photostability of the sunscreen composition is adversely affected if the composition does not retain at least 85% of its initial UV absorbance over the range of 290 nm to 400 nm after being irradiated with 15 MEDs of simulated solar radiation as described hereinbelow.

In order to reduce photochemical reactions that degrade avobenzone, the compositions of the present invention contain at least four EEQs. While not wishing to be bound by a theory, the inventors believe that the inclusion of at least four EEQs within the indicated concentration ranges allows the triplet-excited state energy of avobenzone to be quenched faster than photodegradative chemical reactions can take place in the absence of all four EEQs required by the present invention.

The at least one dibenzoylmethane derivative is selected from the group consisting of:
(a) 2-methyldibenzoylmethane;
(b) 4-methyldibenzoylmethane;
(c) 4-isopropyldibenzoylmethane;
(d) 4-tert-butyldibenzoylmethane;
(e) 2,4-dimethyldibenzoylmethane;
(f) 2,5-dimethyldibenzoylmethane;
(g) 4-tert-butyl-4'-methoxy-dibenzoylmethane;
(h) 4,4'-diisopropyldibenzoylmethane;
(i) 2-methyl-5-isopropyl-4'-methoxydibenzoylmethane;
(j) 2-methyl-5-tert-butyl-4'-methoxydibenzoylmethane;
(k) 2,4-dimethyl-4'-methoxydibenzoylmethane; and
(l) 2,6-dimethyl-4-tert-butyl-4'-methoxydibenzoylmethane In a particularly preferred embodiment of this aspect of the present invention, the at least one dibenzoylmethane derivative is avobenzone, 4-tert-butyl-4'-methoxy dibenzoylmethane. Avobenzone, the USAN name for butylmethoxydibenzoylmethane, is sold under various tradenames, including Parsol® 1789 from DSM.

A dibenzoylmethane derivative is preferably included in the photostable sunscreen compositions of the present invention at concentrations of from about 2.7% to about 3.3%.

The at least four EEQs required in the present invention include octocrylene, oxybenzone, polysilicone-15, and at least one microalgal extract, preferably *Haematococcus pluvialis*.

Oxybenzone, also known as benzophenone-3, is sold under various tradenames including Uvinul® M-40 from BASF and is preferably included in the photostable sunscreen compositions of the present invention at concentrations of from about 5.4% to about 6.6%.

Octocrylene, 2-cyano-3,3-diphenylacrylic acid, is commercially-available from a number of raw material suppliers including Parsol® 340 from DSM. In the photostable sunscreen compositions of the present invention, octocrylene is preferably present at concentrations of from about 2.5% to about 3.1%.

Polysilicone-15 [α-(trimethylsilyl)-w-(trimethylsilyloxy) poly[oxy(dimethyl) silylene]-co-[oxy(methyl)(2-{4-[2,2-bis (ethoxycarbonyl)vinyl]phenoxy}-1-methyleneethyl) silylene]-co-[oxy(methyl)(2-(4-[2,2-bis(ethoxycarbonyl)vinyl]phenoxy)prop-1-enyl)silylene]] is commercially available tradename Parsol® SLX from DSM. In the photostable sunscreen compositions of the present invention, Polysilicone-15 is present at concentrations of from about 0.1% to about 1.0%. Preferably, the photostable sunscreen composition of the present invention contains Polysilicone-15 in a ratio to avobenzone of about 1:3.

One of the required at least four EEQ ingredients is a microalgal extract, preferably an extract of *Haematococcus pluvialis*, which is preferably present at a concentration of from 0.001% to 0.5%. An extract of *H. pluvialis* can be oil-soluble. Such an oil-soluble extract is commercially available from Biosil Technologies under the tradename Astaplancton® G8 (INCI Name: sunflower seed oil (and) *Haematococcus pluvialis* extract). A suitable extract of *H. pluvialis* can also be water-soluble. Such a water-soluble extract is commercially available from Biosil Technologies under the tradename Astaplancton® (INCI Name: water (and) *Haematococcus pluvialis* extract (and) sea water).

In a preferred embodiment, the photostable sunscreen composition of the invention further includes at least one ester, preferably two esters, of salicylic acid that absorb(s) UVR and selected from the group of octisalate, homosalate, as well as octyl, amyl, phenyl, benzyl, glyceryl, and dipropyleneglycol salycilate esters. The at least one salicylate ester is present in the photostable compositions of the present invention at concentrations of from about 4.5% to about 16.5%.

In a particularly preferred embodiment, the at least one ester of salicylic acid that absorbs UVR is selected from the group of homosalate and octisalate.

In an even more preferred embodiment, the photostable composition of the invention contains two salicylate esters, preferably homosalate and octisalate, at a combined concentration of from about 13.5% to about 16.5%.

In addition to a dibenzoylmethane derivative and the optional but preferred two salicylate esters, the photostable sunscreens of the present invention may include one or more additional UVR-absorbing organic filters. As will be appreciated by those of skill in the art, different filters are approved by different regulatory agencies. Among the additional organic sunscreen filters suitable for use in the composition of the present invention are those disclosed in U.S. Pat. Nos. 7,235,587 and 6,444,195 and US Patent Application Publication No. 2007/0140997. The '587 patent refers to sunscreen filters as "photoactive" compounds. For purposes of the present application "photoactive compounds" are to be understood to be synonymous with sunscreen filters.

The photostable sunscreens of the present invention may also contain one or more of the following: Bis-Ethylhexyloxyphenol Methoxyphenyl Triazine (tradename Tinosorb® S from CIBA Specialty Chemicals, High Point, N.C.); Methylene Bis-Benzotriazolyl Tetramethylbutylphenol (tradename Tinosorb® M from CIBA Specialty Chemicals); Butyloctyl Salicylate (tradename HallBrite® BHB from The HallStar Company, Bedford Park, Ill.); Hexadecyl Benzoate; Terephthalylidene Dicamphor Sulfonic Acid (tradename Mexoryl® SX); Diethylhexyl 2,6-Naphthalate (tradename Corapan®TQ from Symrise Inc., Teterboro, N.J.); Diethylhexyl Syringylidene Malonate (tradename Oxynex® ST from EMD Chemicals Inc. Hawthorne, N.Y.); Polyester-8 (tradename Polycrylene® from The HallStar Company); (j) Dimethyl Capramide (tradename SpectraSoly® DMDA from The HallStar Company); and 4-Methylbenzylidene camphor.

The following formulation is illustrative of the photostable sunscreen composition of the present invention and was prepared using techniques and equipment known to those having ordinary skill in the art of formulating personal care products.

Example

Formulation #1 (Photostable Sunscreen of Present Invention)

| INCI Name | Weight % | Weight % (Range) |
|---|---|---|
| Octisalate | 5.00% | 4.50-5.50% |
| Homosalate | 10.0% | 9.00-11.00% |
| Avobenzone | 3.0% | 2.70-3.30% |
| Octocrylene | 2.79% | 2.511-3.069% |
| Oxybenzone | 6.0% | 5.40-6.60% |
| *Haemalococcus pluvialis* Extract | 0.10% | 0.001-0.50% |
| Polysilicone-15 | 0.90% | 0.10-1.00% |
| $C_{12-15}$ Alkyl Benzoate | 8.00% | 3.00-10.00% |
| Tribehenin PEG-20 Esters | 0.60% | 0.20-2.00% |
| Cyclopentasiloxane | 5.00% | 2.00-10.00% |
| *Helianthus Annus* (Sunflower) Seed Oil | 0.50% | 0.10-1.50% |
| Carbomer | 0.50% | 0.10-1.00% |
| Silica | 4.00% | 1.00-8.00% |
| Cetearyl Alcohol | 1.40% | 1.00-3.00% |
| Glyceryl Stearate (and) PEG-100 Stearate | 0.80% | 0.20-2.00% |
| Potassium Cetyl Phosphate | 0.80% | 0.50-2.00% |
| Propanediol | 2.00% | 1.00-4.00% |
| Aminomethyl Propanol | 0.40% | 0.10-1.00% |
| Retinyl Palmitate (and) *Zea Mays* (Corn) Oil (and) Cholecalciferol | 0.10% | 0.01-0.50% |
| Sodium Phytate | 0.10% | .01-0.20% |
| Phenoxyethanol (and) Caprylyl Glycol (and) Chlorphenesin | 1.00% | 0.50-1.30% |
| Water (Aqua) | QS | QS |

Example

Photostability Test #1

Formulation #1 was subjected to photostability testing in three separate studies, described in detail below, to determine the retention of UV protection as a function of time when the formulation is exposed to simulated sunlight. A sunscreen standard, COLIPA P2 SPF 15, was used as a control reference in one or more of the tests. The P2 standard contains Padimate O (7%) and Oxybenzone (3%).

Photostability was determined using an Optometrics LLC Model SPF 290S UV analyzer system. Photostability was judge by the retention of absorbance of UVA radiation, UVB radiation, or both (full spectrum analysis) after exposing the sample to 15 MED (minimal erythema) dose; 1 MED≈20 mJ/cm$^2$).

Samples of the photostable sunscreen composition of the present invention were applied to PMMA (poly(methymethacrylate)) plates (supplied by Schongerg, Hamburg, Germany) as a film at a concentration of 2 mg/cm$^2$. In a first study, the samples of the composition of the present invention were irradiated with simulated natural sunlight to 15 MEDs as emitted by a Solar Light Model ISS Xenon Arc Solar Simulator equipped with Solar Light Dose Control System and UVB detector. (The Solar Simulator was calibrated to meet the common international SPF methodology jointly promulgated by the European Cosmetics Association ("COLIPA"), the Japan Cosmetic Industry Association, the Cosmetic, Toiletry and Fragrance Association of South Africa, published on May 2006, referred to herein as the "COLIPA standard.") The dose control and detector systems were also calibrated. The amount of energy transmitted through the composition of the present invention was recorded initially and then at intervals until 15 MEDs had been administered. The SPF at each interval was calculated by dividing the amount of energy transmitted through a blank film by the amount transmitted through the product-coated film.

A photolabile sunscreen formula containing 6 wt-% octinoxate and 3 wt % avobenzone was used as a "control" sample in the first study.

In the first phase of the first study, the samples were irradiated with the amount of energy transmitted through the product film recorded initially (i.e., at time=0) and then periodically during irradiation with simulated natural sunlight to 15 MEDs produced by a Solar Light Model 15S Xenon Arc Solar Simulator equipped with a Solar Light Dose Control system including a UVB detector. The second phase of the first study was similar to the first phase except a Solar Light Model 601 Multiport Xenon Arc Solar Simulator was used for irradiation. The Solar Simulator was filtered to provide a UVA spectra meeting the Persistent Pigment Darkening specifications promulgated by the Japan Cosmetic Industry Association (JCIA). See, Japan Cosmetic Industry Association Measurement Standard for UVA Protection Efficacy (1995) at www.jcia.org. The energy transmitted in mw/cm$^2$ was recorded initially and periodically up to an amount of energy equal to about 600 mw/cm$^2$, or approximately 4 theoretical PPDs.

The results of the first photostability study were as follows.

Tables 1.1-1.2 show the SPF values and associated percent erythemal energy transmittance through the photostable sunscreen composition of the present invention and the COLIPA P2 SPF 15 Standard.

TABLE 1.1

| Formulation #1 | | | | | | | | | |
|---|---|---|---|---|---|---|---|---|---|
| | Trial 1 | Trial 2 | Trial 3 | Trial 4 | Trial 5 | Trial 6 | Average MED/hr | Average SPF | Percent Transmittance |
| Initial | 0.5 | 0.4 | 0.5 | 0.8 | 0.6 | 0.7 | 0.58 | 150.86 | 0.66 |
| 30 | 0.5 | 0.4 | 0.5 | 0.7 | 0.5 | 0.6 | 0.53 | 165.00 | 0.61 |
| 60 | 0.5 | 0.3 | 0.5 | 0.7 | 0.5 | 0.6 | 0.52 | 170.32 | 0.59 |
| 90 | 0.5 | 0.3 | 0.5 | 0.7 | 0.5 | 0.6 | 0.52 | 170.32 | 0.59 |
| 120 | 0.5 | 0.3 | 0.5 | 0.7 | 0.5 | 0.5 | 0.50 | 176.00 | 0.57 |
| 150 | 0.5 | 0.3 | 0.5 | 0.7 | 0.5 | 0.5 | 0.50 | 176.00 | 0.57 |
| 180 | 0.5 | 0.3 | 0.5 | 0.7 | 0.5 | 0.6 | 0.52 | 170.32 | 0.59 |
| 210 | 0.5 | 0.3 | 0.5 | 0.7 | 0.5 | 0.6 | 0.52 | 170.32 | 0.59 |
| 240 | 0.5 | 0.3 | 0.5 | 0.7 | 0.5 | 0.6 | 0.52 | 170.32 | 0.59 |
| 270 | 0.5 | 0.4 | 0.5 | 0.7 | 0.5 | 0.6 | 0.53 | 165.00 | 0.61 |
| 300 | 0.5 | 0.4 | 0.5 | 0.7 | 0.5 | 0.6 | 0.53 | 165.00 | 0.61 |

TABLE 1.2

COLIPA P2 SPF 15 Standard

|  | Trial 1 | Trial 2 | Trial 3 | Trial 4 | Trial 5 | Trial 6 | Average MED/hr | Average SPF | Percent Transmittance |
|---|---|---|---|---|---|---|---|---|---|
| Initial | 1.2 | 0.6 | 1.1 | 0.4 | 0.3 | 0.4 | 0.67 | 132.00 | 0.76 |
| 30 | 2.3 | 2.2 | 3.8 | 1 | 0.8 | 3.3 | 2.23 | 39.40 | 2.54 |
| 60 | 5.1 | 5 | 6.2 | 3 | 2.1 | 5.1 | 4.42 | 19.92 | 5.02 |
| 90 | 7.9 | 7.8 | 11.5 | 4.9 | 4.4 | 8.4 | 7.48 | 11.76 | 8.50 |
| 120 | 10.4 | 10.3 | 14.5 | 7 | 6.3 | 11.5 | 10.00 | 8.80 | 11.36 |
| 150 | 12.6 | 12.5 | 16.9 | 9 | 9 | 11.8 | 11.97 | 7.35 | 13.60 |
| 180 | 15 | 14.6 | 19.2 | 11 | 10.2 | 14.3 | 14.05 | 6.26 | 15.97 |
| 210 | 15.8 | 16.4 | 21.2 | 12.7 | 12.2 | 16.3 | 15.77 | 5.58 | 17.92 |
| 240 | 18 | 18.3 | 23.2 | 14.4 | 13.8 | 18.1 | 17.63 | 4.99 | 20.04 |
| 270 | 20.1 | 20.2 | 24.8 | 15.9 | 12.8 | 21.1 | 19.15 | 4.60 | 21.76 |
| 300 | 22.2 | 21.7 | 26.6 | 17.5 | 16.6 | 22.9 | 21.25 | 4.14 | 24.15 |

Table 1.3 shows the persistent pigment darkening (PPD) values and associated transmittance values during irradiation with a "UVA" PPD test type spectra in accordance with JCIA standard.

TABLE 1.3

PPD of Formulation #1

| Mins | Trial 1 | Trial 2 | Trial 3 | Trial 4 | Trial 5 | Trial 6 | Avg | Estimated PPD |
|---|---|---|---|---|---|---|---|---|
| 0 | 0.77 | 0.94 | 0.85 | 0.9 | 0.86 | 1.01 | 0.88 | 56.7 |
| 3 | 0.97 | 1.23 | 0.82 | 0.88 | 0.91 | 1.1 | 0.99 | 50.8 |
| 6 | 1.02 | 1.24 | 0.93 | 1 | 1 | 1.18 | 1.06 | 47.1 |
| 9 | 1.06 | 1.36 | 0.9 | 0.79 | 1.06 | 1.19 | 1.06 | 47.2 |
| 12 | 1.1 | 1.19 | 1.15 | 0.91 | 1.03 | 1.32 | 1.12 | 44.8 |
| 15 | 1.15 | 1.26 | 1.19 | 1.11 | 1.11 | 1.38 | 1.2 | 41.7 |
| 18 | 1.35 | 1.46 | 1.09 | 1.02 | 1.12 | 1.35 | 1.23 | 40.6 |
| 21 | 1.43 | 1.24 | 1.21 | 1.2 | 1.15 | 1.35 | 1.26 | 39.6 |

In the above tests, it should be noted that to twenty-one minutes of UVA energy, at an applied dose of 100 mw/cm$^2$, used to irradiate the samples is equivalent to about 8.4 theoretical PPDs.

Example 2

Photostability Study

A second photostability study was performed in the same manner as the first study except as follows. A Solar Light Model 601 Multiport Xenon Arc Solar Simulator was filtered to provide a UVA spectra meeting the Persistent Pigment Darkening (PPD) specifications used by the Japanese Cosmetic Industry Association. The administered dose was equal to about 600 mw/cm$^2$, which is equivalent to approximately 4 theoretical PPD units.

COLIPA sunscreen standard P2 SPF 15 ("P2") was used as the control reference in the second study. The results of the second study are given below Sample Identification for Second Photostability Study

| Sample # | Description | |
|---|---|---|
| 1. | Formulation #1 | Initial and Irradiated |
| 2 | Formulation #1 | Initial and Irradiated |
| 3. | Formulation #1 | Initial and Irradiated |
| 4. | Formulation #1 | Initial and Dark Control |
| 5. | Formulation #1 | Initial and Dark Control |

-continued

| Sample # | Description | |
|---|---|---|
| 6. | Formulation #1 | Initial and Dark Control |
| 7. | COLIPA P2 Std | Initial and Irradiated |
| 8. | COLIPA P2 Std | Initial and Irradiated |
| 9. | COLIPA P2 Std | Initial and Irradiated |
| 10. | COLIPA P2 Std | Initial and Dark Control |
| 11. | COLIPA P2 Std | Initial and Dark Control |
| 12. | COLIPA P2 Std | Initial and Dark Control |
| 13. | Formulation #1 | Initial and Dark Heated Control |
| 14. | Formulation #1 | Initial and Dark Heated Control |
| 15. | Formulation #1 | Initial and Dark Heated Control |
| 16. | COLIPA P2 Std | Initial and Dark Heated Control |
| 17. | COLIPA P2 Std | Initial and Dark Heated Control |

The initial and post-irradiation % absorbance for Samples 1-3 are shown in Tables 2.1-2.3.

TABLE 2.1

Sample 1

| Wavelength | Initial | After Irradiation | % Retained |
|---|---|---|---|
| 290 | 1.919 | 1.735 | 90.4 |
| 295 | 1.897 | 1.708 | 90.0 |
| 300 | 1.84 | 1.67 | 90.8 |
| 305 | 1.833 | 1.66 | 90.6 |
| 310 | 1.846 | 1.659 | 89.9 |
| 315 | 1.867 | 1.68 | 90.0 |
| 320 | 1.873 | 1.677 | 89.5 |
| 325 | 1.832 | 1.645 | 89.8 |
| 330 | 1.791 | 1.601 | 89.4 |
| 335 | 1.758 | 1.58 | 89.9 |
| 340 | 1.744 | 1.563 | 89.6 |
| 345 | 1.713 | 1.53 | 89.3 |
| 350 | 1.671 | 1.498 | 89.6 |
| 355 | 1.636 | 1.459 | 89.2 |
| 360 | 1.586 | 1.413 | 89.1 |
| 365 | 1.515 | 1.347 | 88.9 |
| 370 | 1.405 | 1.25 | 89.0 |
| 375 | 1.296 | 1.154 | 89.0 |
| 380 | 1.204 | 1.068 | 88.7 |
| 385 | 0.999 | 0.881 | 88.2 |
| 390 | 0.615 | 0.542 | 88.1 |
| 395 | 0.273 | 0.243 | 89.0 |
| 400 | 0.116 | 0.107 | 92.2 |

TABLE 2.2

Sample 2

| Wavelength | Initial | After Irradiation | % Retained |
|---|---|---|---|
| 290 | 1.956 | 1.699 | 86.9 |
| 295 | 1.933 | 1.689 | 87.4 |
| 300 | 1.877 | 1.643 | 87.5 |
| 305 | 1.861 | 1.628 | 87.5 |
| 310 | 1.883 | 1.641 | 87.1 |
| 315 | 1.902 | 1.645 | 86.5 |
| 320 | 1.912 | 1.643 | 85.9 |
| 325 | 1.871 | 1.611 | 86.1 |
| 330 | 1.815 | 1.581 | 87.1 |
| 335 | 1.788 | 1.56 | 87.2 |
| 340 | 1.769 | 1.54 | 87.1 |
| 345 | 1.751 | 1.511 | 86.3 |
| 350 | 1.701 | 1.473 | 86.6 |
| 355 | 1.665 | 1.442 | 86.6 |
| 360 | 1.616 | 1.396 | 86.4 |
| 365 | 1.544 | 1.334 | 86.4 |
| 370 | 1.434 | 1.239 | 86.4 |
| 375 | 1.327 | 1.148 | 86.5 |
| 380 | 1.233 | 1.066 | 86.5 |
| 385 | 1.026 | 0.888 | 86.5 |
| 390 | 0.637 | 0.56 | 87.9 |
| 395 | 0.289 | 0.26 | 90.0 |
| 400 | 0.125 | 0.122 | 97.6 |

TABLE 2.3

Sample 3

| Wavelength | Initial | After Irradiation | % Retained |
|---|---|---|---|
| 290 | 2.212 | 1.872 | 84.6 |
| 295 | 2.105 | 1.849 | 87.8 |
| 300 | 2.062 | 1.798 | 87.2 |
| 305 | 2.035 | 1.792 | 88.1 |
| 310 | 2.049 | 1.786 | 87.2 |
| 315 | 2.096 | 1.816 | 86.6 |
| 320 | 2.113 | 1.813 | 85.8 |
| 325 | 2.08 | 1.782 | 85.7 |
| 330 | 2.029 | 1.756 | 86.5 |
| 335 | 2.006 | 1.722 | 85.8 |
| 340 | 1.98 | 1.711 | 86.4 |
| 345 | 1.947 | 1.677 | 86.1 |
| 350 | 1.906 | 1.642 | 86.1 |
| 355 | 1.868 | 1.6 | 85.7 |
| 360 | 1.815 | 1.554 | 85.6 |
| 365 | 1.736 | 1.486 | 85.6 |
| 370 | 1.615 | 1.386 | 85.8 |
| 375 | 1.497 | 1.29 | 86.2 |
| 380 | 1.394 | 1.198 | 85.9 |
| 385 | 1.162 | 1.002 | 86.2 |
| 390 | 0.72 | 0.628 | 87.2 |
| 395 | 0.321 | 0.286 | 89.1 |
| 400 | 0.136 | 0.126 | 92.6 |

The initial and post-irradiation % absorbance for the P2 standard are shown in Tables 2.4-2.6.

TABLE 2.4

Sample 7

| Wavelength | Initial | After Irradiation | % Retained |
|---|---|---|---|
| 290 | 1.606 | 1.467 | 91.3 |
| 295 | 1.628 | 1.465 | 90.0 |
| 300 | 1.635 | 1.441 | 88.1 |
| 305 | 1.632 | 1.437 | 88.1 |
| 310 | 1.635 | 1.429 | 87.4 |
| 315 | 1.617 | 1.394 | 86.2 |

TABLE 2.4-continued

Sample 7

| Wavelength | Initial | After Irradiation | % Retained |
|---|---|---|---|
| 320 | 1.508 | 1.284 | 85.1 |
| 325 | 1.317 | 1.118 | 84.9 |
| 330 | 1.113 | 0.963 | 86.5 |
| 335 | 0.95 | 0.842 | 88.6 |
| 340 | 0.833 | 0.749 | 89.9 |
| 345 | 0.731 | 0.656 | 89.7 |
| 350 | 0.623 | 0.558 | 89.6 |
| 355 | 0.521 | 0.456 | 87.5 |
| 360 | 0.413 | 0.35 | 84.7 |
| 365 | 0.316 | 0.257 | 81.3 |
| 370 | 0.238 | 0.183 | 76.9 |
| 375 | 0.177 | 0.125 | 70.6 |
| 380 | 0.137 | 0.089 | 65.0 |
| 385 | 0.108 | 0.063 | 58.3 |
| 390 | 0.091 | 0.051 | 56.0 |
| 395 | 0.079 | 0.039 | 49.4 |
| 400 | 0.073 | 0.034 | 46.6 |

TABLE 2.5

Sample 8

| Wavelength | Initial | After Irradiation | % Retained |
|---|---|---|---|
| 290 | 1.564 | 1.422 | 90.9 |
| 295 | 1.593 | 1.42 | 89.1 |
| 300 | 1.578 | 1.393 | 88.3 |
| 305 | 1.6 | 1.391 | 86.9 |
| 310 | 1.601 | 1.383 | 86.4 |
| 315 | 1.577 | 1.341 | 85.0 |
| 320 | 1.466 | 1.233 | 84.1 |
| 325 | 1.279 | 1.072 | 83.8 |
| 330 | 1.081 | 0.919 | 85.0 |
| 335 | 0.92 | 0.8 | 87.0 |
| 340 | 0.806 | 0.71 | 88.1 |
| 345 | 0.702 | 0.621 | 88.5 |
| 350 | 0.6 | 0.529 | 88.2 |
| 355 | 0.5 | 0.433 | 86.6 |
| 360 | 0.395 | 0.335 | 84.8 |
| 365 | 0.304 | 0.248 | 81.6 |
| 370 | 0.231 | 0.18 | 77.9 |
| 375 | 0.173 | 0.128 | 74.0 |
| 380 | 0.136 | 0.094 | 69.1 |
| 385 | 0.11 | 0.07 | 63.6 |
| 390 | 0.097 | 0.058 | 59.8 |
| 395 | 0.084 | 0.048 | 57.1 |
| 400 | 0.079 | 0.042 | 53.2 |

TABLE 2.6

Sample 9

| Wavelength | Initial | After Irradiation | % Retained |
|---|---|---|---|
| 290 | 1.697 | 1.59 | 93.7 |
| 295 | 1.727 | 1.592 | 92.2 |
| 300 | 1.716 | 1.555 | 90.6 |
| 305 | 1.725 | 1.538 | 89.2 |
| 310 | 1.717 | 1.552 | 90.4 |
| 315 | 1.712 | 1.507 | 88.0 |
| 320 | 1.597 | 1.398 | 87.5 |
| 325 | 1.414 | 1.226 | 86.7 |
| 330 | 1.197 | 1.054 | 88.1 |
| 335 | 1.025 | 0.919 | 89.7 |
| 340 | 0.9 | 0.817 | 90.8 |
| 345 | 0.785 | 0.715 | 91.1 |
| 350 | 0.672 | 0.608 | 90.5 |
| 355 | 0.555 | 0.494 | 89.0 |

TABLE 2.6-continued

Sample 9

| Wavelength | Initial | After Irradiation | % Retained |
|---|---|---|---|
| 360 | 0.434 | 0.378 | 87.1 |
| 365 | 0.325 | 0.274 | 84.3 |
| 370 | 0.239 | 0.194 | 81.2 |
| 375 | 0.171 | 0.13 | 76.0 |
| 380 | 0.128 | 0.089 | 69.5 |
| 385 | 0.096 | 0.063 | 65.6 |
| 390 | 0.08 | 0.049 | 61.3 |
| 395 | 0.066 | 0.037 | 56.1 |
| 400 | 0.06 | 0.032 | 53.3 |

Tables 2.7, 2.8, and 2.9 indicate the difference between the initial experimental values and the change in absorbance after storage for about 45 minutes in a dark oven heated to about 100° F. As used herein "dark sample" means is a one that is stored in the dark for approximately the same time as identical samples were irradiated.

TABLE 2.7

Sample 13 (Average of 4 Scans)

| Wavelength | Initial | Dark/Heat | % Retained |
|---|---|---|---|
| 290 | 1.822 | 1.788 | 98.13 |
| 295 | 1.796 | 1.771 | 98.61 |
| 300 | 1.762 | 1.717 | 97.45 |
| 305 | 1.753 | 1.714 | 97.78 |
| 310 | 1.762 | 1.715 | 97.33 |
| 315 | 1.782 | 1.737 | 97.47 |
| 320 | 1.778 | 1.739 | 97.81 |
| 325 | 1.74 | 1.701 | 97.76 |
| 330 | 1.693 | 1.66 | 98.05 |
| 335 | 1.658 | 1.618 | 97.59 |
| 340 | 1.64 | 1.607 | 97.99 |
| 345 | 1.615 | 1.583 | 98.02 |
| 350 | 1.58 | 1.541 | 97.53 |
| 355 | 1.544 | 1.501 | 97.22 |
| 360 | 1.498 | 1.461 | 97.53 |
| 365 | 1.431 | 1.386 | 96.86 |
| 370 | 1.326 | 1.283 | 96.76 |
| 375 | 1.227 | 1.186 | 96.66 |
| 380 | 1.136 | 1.097 | 96.57 |
| 385 | 0.942 | 0.903 | 95.86 |
| 390 | 0.584 | 0.549 | 94.01 |
| 395 | 0.269 | 0.245 | 91.08 |
| 400 | 0.123 | 0.109 | 88.62 |

TABLE 2.8

Sample 14 (Average of 4 Scans)

| Wavelength | Initial | Dark/Heat | % Retained |
|---|---|---|---|
| 290 | 1.85 | 1.78 | 96.22 |
| 295 | 1.807 | 1.796 | 99.39 |
| 300 | 1.778 | 1.757 | 98.82 |
| 305 | 1.774 | 1.74 | 98.08 |
| 310 | 1.791 | 1.75 | 97.71 |
| 315 | 1.795 | 1.766 | 98.38 |
| 320 | 1.798 | 1.755 | 97.61 |
| 325 | 1.756 | 1.739 | 99.03 |
| 330 | 1.717 | 1.683 | 98.02 |
| 335 | 1.689 | 1.653 | 97.87 |
| 340 | 1.665 | 1.643 | 98.68 |
| 345 | 1.634 | 1.61 | 98.53 |
| 350 | 1.604 | 1.571 | 97.94 |
| 355 | 1.566 | 1.535 | 98.02 |
| 360 | 1.519 | 1.49 | 98.09 |
| 365 | 1.453 | 1.419 | 97.66 |
| 370 | 1.347 | 1.315 | 97.62 |

TABLE 2.8-continued

Sample 14 (Average of 4 Scans)

| Wavelength | Initial | Dark/Heat | % Retained |
|---|---|---|---|
| 375 | 1.246 | 1.217 | 97.67 |
| 380 | 1.156 | 1.125 | 97.32 |
| 385 | 0.957 | 0.925 | 96.66 |
| 390 | 0.594 | 0.568 | 95.62 |
| 395 | 0.276 | 0.257 | 93.12 |
| 400 | 0.126 | 0.116 | 92.06 |

TABLE 2.9

Sample 15 (Average of 4 Scans)

| Wavelength | Initial | Dark/Heat | % Retained |
|---|---|---|---|
| 290 | 2.038 | 2.006 | 98.43 |
| 295 | 2.032 | 1.949 | 95.92 |
| 300 | 1.955 | 1.9 | 97.19 |
| 305 | 1.959 | 1.882 | 96.07 |
| 310 | 1.967 | 1.895 | 96.34 |
| 315 | 1.992 | 1.922 | 96.49 |
| 320 | 1.999 | 1.929 | 96.50 |
| 325 | 1.972 | 1.889 | 95.79 |
| 330 | 1.913 | 1.85 | 96.71 |
| 335 | 1.891 | 1.81 | 95.72 |
| 340 | 1.87 | 1.797 | 96.10 |
| 345 | 1.843 | 1.768 | 95.93 |
| 350 | 1.801 | 1.724 | 95.72 |
| 355 | 1.759 | 1.685 | 95.79 |
| 360 | 1.705 | 1.634 | 95.84 |
| 365 | 1.629 | 1.561 | 95.83 |
| 370 | 1.513 | 1.45 | 95.84 |
| 375 | 1.401 | 1.34 | 95.65 |
| 380 | 1.298 | 1.245 | 95.92 |
| 385 | 1.074 | 1.028 | 95.72 |
| 390 | 0.663 | 0.63 | 95.02 |
| 395 | 0.3 | 0.282 | 94.00 |
| 400 | 0.133 | 0.124 | 93.23 |

Tables 2.10, 2.11, and 2.12 show the initial and values after storage at approximately 100° F. for 45 minutes.

TABLE 2.10

Sample 16

| Wavelength | Initial | After Irradiation | % Retained |
|---|---|---|---|
| 295 | 1.518 | 1.436 | 94.6 |
| 300 | 1.512 | 1.437 | 95.0 |
| 305 | 1.524 | 1.447 | 94.9 |
| 310 | 1.519 | 1.442 | 94.9 |
| 315 | 1.485 | 1.409 | 94.9 |
| 320 | 1.364 | 1.292 | 94.7 |
| 325 | 1.174 | 1.117 | 95.1 |
| 330 | 0.982 | 0.937 | 95.4 |
| 335 | 0.834 | 0.8 | 95.9 |
| 340 | 0.727 | 0.702 | 96.6 |
| 345 | 0.632 | 0.612 | 96.8 |
| 350 | 0.539 | 0.52 | 96.5 |
| 355 | 0.444 | 0.43 | 96.8 |
| 360 | 0.347 | 0.334 | 96.3 |
| 365 | 0.263 | 0.25 | 95.1 |
| 370 | 0.194 | 0.184 | 94.8 |
| 375 | 0.139 | 0.131 | 94.2 |
| 380 | 0.103 | 0.095 | 92.2 |
| 385 | 0.081 | 0.071 | 87.7 |
| 390 | 0.065 | 0.058 | 89.2 |
| 395 | 0.053 | 0.046 | 86.8 |
| 400 | 0.048 | 0.043 | 89.6 |

TABLE 2.11

Sample 17 (P2 Standard; Dark/Heated)

| Wavelength | Initial | After Irradiation | % Retained |
|---|---|---|---|
| 290 | 1.568 | 1.476 | 94.1 |
| 295 | 1.591 | 1.5 | 94.3 |
| 300 | 1.587 | 1.501 | 94.6 |
| 305 | 1.598 | 1.506 | 94.2 |
| 310 | 1.6 | 1.502 | 93.9 |
| 315 | 1.573 | 1.469 | 93.4 |
| 320 | 1.448 | 1.354 | 93.5 |
| 325 | 1.248 | 1.166 | 93.4 |
| 330 | 1.043 | 0.979 | 93.9 |
| 335 | 0.881 | 0.831 | 94.3 |
| 340 | 0.765 | 0.725 | 94.8 |
| 345 | 0.663 | 0.631 | 95.2 |
| 350 | 0.561 | 0.533 | 95.0 |
| 355 | 0.461 | 0.436 | 94.6 |
| 360 | 0.358 | 0.337 | 94.1 |
| 365 | 0.268 | 0.25 | 93.3 |
| 370 | 0.197 | 0.182 | 92.4 |
| 375 | 0.143 | 0.127 | 88.8 |
| 380 | 0.105 | 0.092 | 87.6 |
| 385 | 0.081 | 0.068 | 84.0 |
| 390 | 0.067 | 0.055 | 82.1 |
| 395 | 0.055 | 0.041 | 74.5 |
| 400 | 0.049 | 0.04 | 81.6 |

TABLE 2.12

Sample 18 (P2 Standard; Dark/Heated)

| Wavelength | Initial | After Irradiation | % Retained |
|---|---|---|---|
| 295 | 1.601 | 1.573 | 98.3 |
| 300 | 1.595 | 1.565 | 98.1 |
| 305 | 1.6 | 1.579 | 98.7 |
| 310 | 1.606 | 1.576 | 98.1 |
| 315 | 1.566 | 1.546 | 98.7 |
| 320 | 1.456 | 1.423 | 97.7 |
| 325 | 1.259 | 1.229 | 97.6 |
| 330 | 1.057 | 1.034 | 97.8 |
| 335 | 0.898 | 0.883 | 98.3 |
| 340 | 0.783 | 0.771 | 98.5 |
| 345 | 0.683 | 0.674 | 98.7 |
| 350 | 0.581 | 0.569 | 97.9 |
| 355 | 0.477 | 0.465 | 97.5 |
| 360 | 0.371 | 0.36 | 97.0 |
| 365 | 0.277 | 0.264 | 95.3 |
| 370 | 0.2 | 0.191 | 95.5 |
| 375 | 0.141 | 0.132 | 93.6 |
| 380 | 0.101 | 0.093 | 92.1 |
| 385 | 0.074 | 0.068 | 91.9 |
| 390 | 0.06 | 0.054 | 90.0 |
| 395 | 0.047 | 0.042 | 89.4 |
| 400 | 0.042 | 0.039 | 92.9 |

Table 2.13 below shows the initial and post-irradiation absorbance of the control samples.

Dark Heated Control Correction Factor

| Wavelength | Sample 13 % Retained | Sample % Retained 14 | Sample 15 % Retained | Average % Retained |
|---|---|---|---|---|
| 290 | 98.13 | 96.22 | 98.43 | 97.59 |
| 295 | 98.61 | 99.39 | 95.92 | 97.97 |
| 300 | 97.45 | 98.82 | 97.19 | 97.82 |
| 305 | 97.78 | 98.08 | 96.07 | 97.31 |
| 310 | 97.33 | 97.71 | 96.34 | 97.13 |
| 315 | 97.47 | 98.38 | 96.49 | 97.45 |
| 320 | 97.81 | 97.61 | 96.50 | 97.30 |
| 325 | 97.76 | 99.03 | 95.79 | 97.53 |
| 330 | 98.05 | 98.02 | 96.71 | 97.59 |
| 335 | 97.59 | 97.87 | 95.72 | 97.06 |
| 340 | 97.99 | 98.68 | 96.10 | 97.59 |
| 345 | 98.02 | 98.53 | 95.93 | 97.49 |
| 350 | 97.53 | 97.94 | 95.72 | 97.07 |
| 355 | 97.22 | 98.02 | 95.79 | 97.01 |
| 360 | 97.53 | 98.09 | 95.84 | 97.15 |
| 365 | 96.86 | 97.66 | 95.83 | 96.78 |
| 370 | 96.76 | 97.62 | 95.84 | 96.74 |
| 375 | 96.66 | 97.67 | 95.65 | 96.66 |
| 380 | 96.57 | 97.32 | 95.92 | 96.60 |
| 385 | 95.86 | 96.66 | 95.72 | 96.08 |
| 390 | 94.01 | 95.62 | 95.02 | 94.88 |
| 395 | 91.08 | 93.12 | 94.00 | 92.73 |
| 400 | 88.62 | 92.06 | 93.23 | 91.30 |

Table 2.14 shows the P2 standard corrected absorbance after irradiation.

TABLE 2.14

Experimental Average Absorbance Retained

| Wavelength | Average % Retained | % Correction Factor | Correct Absorbance |
|---|---|---|---|
| 290 | 87.3 | 97.59 | 89.45 |
| 295 | 88.4 | 97.97 | 90.25 |
| 300 | 88.5 | 97.82 | 90.47 |
| 305 | 88.7 | 97.31 | 91.15 |
| 310 | 88.1 | 97.13 | 90.67 |
| 315 | 87.7 | 97.45 | 90.00 |
| 320 | 87.1 | 97.30 | 89.50 |
| 325 | 87.2 | 97.53 | 89.40 |
| 330 | 87.7 | 97.59 | 89.84 |
| 335 | 87.7 | 97.06 | 90.31 |
| 340 | 87.7 | 97.59 | 89.86 |
| 345 | 87.2 | 97.49 | 89.49 |
| 350 | 87.5 | 97.07 | 90.11 |
| 355 | 87.1 | 97.01 | 89.83 |
| 360 | 87.0 | 97.15 | 89.58 |
| 365 | 87.0 | 96.78 | 89.86 |
| 370 | 87.1 | 96.74 | 90.00 |
| 375 | 87.2 | 96.66 | 90.26 |
| 380 | 87.0 | 96.60 | 90.10 |
| 385 | 87.0 | 96.08 | 90.54 |
| 390 | 87.8 | 94.88 | 92.49 |
| 395 | 89.4 | 92.73 | 96.36 |
| 400 | 94.2 | 91.30 | 103.13 |

Table 2.15 shows the P2 standard corrected absorbance after irradiation.

TABLE 2.15

Sample Absorbance After Dark Sample Corrections

| Wavelength | Average % Retained | % Correction Factor | Correct Absorbance |
|---|---|---|---|
| 290 | 92.0 | 95.9 | 95.95 |
| 295 | 90.4 | 95.7 | 94.49 |
| 300 | 89.0 | 95.9 | 92.80 |
| 305 | 88.0 | 96.0 | 91.76 |
| 310 | 88.1 | 95.6 | 92.07 |
| 315 | 86.4 | 95.7 | 90.34 |
| 320 | 85.6 | 95.3 | 89.80 |
| 325 | 85.1 | 95.4 | 89.24 |
| 330 | 86.5 | 95.7 | 90.42 |
| 335 | 88.4 | 96.2 | 91.92 |
| 340 | 89.6 | 96.6 | 92.75 |
| 345 | 89.8 | 96.9 | 92.64 |
| 350 | 89.4 | 96.5 | 92.67 |
| 355 | 87.7 | 96.3 | 91.08 |
| 360 | 85.6 | 95.8 | 89.29 |
| 365 | 82.4 | 94.5 | 87.16 |
| 370 | 78.7 | 94.2 | 83.47 |
| 375 | 73.5 | 92.2 | 79.75 |
| 380 | 67.9 | 90.6 | 74.88 |
| 385 | 62.5 | 87.8 | 71.19 |
| 390 | 59.0 | 87.1 | 67.77 |
| 395 | 54.2 | 83.6 | 64.85 |
| 400 | 51.0 | 88.0 | 57.97 |

Table 2.16 shows the Critical Wavelength (CW) and Boots star rating of the photostable sunscreen composition of the present invention both before and after irradiation.

TABLE 2.16

Critical Wavelength and Boots Star Rating

| | Critical Wavelength | | Boots Star Rating | |
|---|---|---|---|---|
| | Initial | Post-Irradiation | Initial | Post-Irradiation |
| Sample 1 | 378.5 | 378.5 | 3 | 3 |
| Sample 2 | 378.6 | 378.6 | 3 | 3 |
| Sample 3 | 378.7 | 378.7 | 3 | 3 |

Example 3

Photostability Study

A third study was conducted to evaluate the photostability of Formulation #1 using the equipment and methods of the second study. The results of the third study are given below.

Sample Identification for Third Photostability Study

| Sample | Code | Description |
|---|---|---|
| 10-021-1 and -1B | Formulation #1 | 1 Initial and 1B |
| 10-021-2 and -2B | Formulation #1 | 2 Initial and 2B Irradiated |
| 10-021-3 & -3B | Formulation #1 | 3 Initial and 3B Irradiated |
| 10-021-4 & -4B | Formulation #1 | 4 Initial and 4B Stored in Dark |
| 10-021-5 and -5B | Formulation #1 | 5 Initial and 5B Stored in Dark |
| 10-021-6 and -6B | Formulation #1 | 6 Initial and 6B Stored in Dark |

TABLE 3.1

Initial and Post-Irradiation Absorbance Formulation #1 (Invention)

| Wavelength (nm) | 10-021-1 | 10-021-2 | 10-021-3 | 10-021-1B | 10-021-2B | 10-021-3B |
|---|---|---|---|---|---|---|
| 290 | 1.738 | 1.899 | 1.994 | 1.571 | 1.639 | 1.805 |
| 295 | 1.723 | 1.864 | 1.957 | 1.529 | 1.611 | 1.783 |
| 300 | 1.678 | 1.823 | 1.913 | 1.502 | 1.578 | 1.726 |
| 305 | 1.669 | 1.804 | 1.887 | 1.484 | 1.552 | 1.704 |
| 310 | 1.679 | 1.821 | 1.915 | 1.473 | 1.558 | 1.71 |
| 315 | 1.7 | 1.847 | 1.938 | 1.501 | 1.576 | 1.737 |
| 320 | 1.69 | 1.844 | 1.951 | 1.504 | 1.579 | 1.734 |
| 325 | 1.657 | 1.821 | 1.899 | 1.467 | 1.559 | 1.703 |
| 330 | 1.611 | 1.764 | 1.856 | 1.45 | 1.531 | 1.687 |
| 335 | 1.587 | 1.733 | 1.824 | 1.434 | 1.512 | 1.664 |
| 340 | 1.561 | 1.71 | 1.8 | 1.402 | 1.493 | 1.635 |
| 345 | 1.542 | 1.697 | 1.785 | 1.383 | 1.473 | 1.615 |
| 350 | 1.504 | 1.659 | 1.742 | 1.352 | 1.438 | 1.572 |
| 355 | 1.465 | 1.615 | 1.693 | 1.309 | 1.399 | 1.532 |
| 360 | 1.423 | 1.571 | 1.641 | 1.267 | 1.357 | 1.483 |
| 365 | 1.359 | 1.501 | 1.567 | 1.208 | 1.295 | 1.412 |
| 370 | 1.26 | 1.395 | 1.45 | 1.118 | 1.208 | 1.31 |
| 375 | 1.166 | 1.294 | 1.341 | 1.035 | 1.121 | 1.211 |
| 380 | 1.076 | 1.201 | 1.237 | 0.954 | 1.037 | 1.116 |
| 385 | 0.893 | 1.005 | 1.025 | 0.79 | 0.872 | 0.925 |
| 390 | 0.547 | 0.623 | 0.624 | 0.488 | 0.552 | 0.567 |
| 395 | 0.248 | 0.285 | 0.281 | 0.23 | 0.263 | 0.259 |
| 400 | 0.108 | 0.126 | 0.123 | 0.11 | 0.13 | 0.123 |

Tables 3.4, 3.5 and 3.6 indicate absorbance of initial and dark samples of Formulation #1 and comparative Commercial Formulation #s 3 and 4.

TABLE 3.4

| Initial and Dark Absorbance Formulation #1 (Invention) | | | | | | |
|---|---|---|---|---|---|---|
| Wavelength (nm) | 10-021-4 | 10-021-5 | 10-021-6 | 10-021-4B | 10-021-5B | 10-021-6B |
| 290 | 1.894 | 1.794 | 1.867 | 1.846 | 1.765 | 1.853 |
| 295 | 1.853 | 1.778 | 1.851 | 1.815 | 1.754 | 1.834 |
| 300 | 1.817 | 1.741 | 1.821 | 1.784 | 1.719 | 1.789 |
| 305 | 1.799 | 1.734 | 1.818 | 1.763 | 1.703 | 1.771 |
| 310 | 1.821 | 1.736 | 1.801 | 1.787 | 1.714 | 1.789 |
| 315 | 1.84 | 1.751 | 1.834 | 1.795 | 1.737 | 1.817 |
| 320 | 1.842 | 1.756 | 1.838 | 1.797 | 1.734 | 1.805 |
| 325 | 1.809 | 1.715 | 1.8 | 1.755 | 1.691 | 1.767 |
| 330 | 1.752 | 1.676 | 1.76 | 1.727 | 1.655 | 1.73 |
| 335 | 1.73 | 1.656 | 1.738 | 1.694 | 1.631 | 1.702 |
| 340 | 1.707 | 1.638 | 1.717 | 1.672 | 1.603 | 1.675 |
| 345 | 1.687 | 1.616 | 1.694 | 1.646 | 1.597 | 1.657 |
| 350 | 1.644 | 1.576 | 1.658 | 1.611 | 1.554 | 1.623 |
| 355 | 1.602 | 1.538 | 1.615 | 1.565 | 1.511 | 1.58 |
| 360 | 1.56 | 1.495 | 1.569 | 1.525 | 1.47 | 1.536 |
| 365 | 1.49 | 1.429 | 1.499 | 1.455 | 1.405 | 1.47 |
| 370 | 1.385 | 1.33 | 1.392 | 1.35 | 1.308 | 1.365 |
| 375 | 1.283 | 1.233 | 1.294 | 1.252 | 1.212 | 1.266 |
| 380 | 1.19 | 1.143 | 1.201 | 1.157 | 1.123 | 1.173 |
| 385 | 0.995 | 0.956 | 1.002 | 0.96 | 0.934 | 0.977 |
| 390 | 0.621 | 0.598 | 0.625 | 0.593 | 0.582 | 0.603 |
| 395 | 0.289 | 0.283 | 0.291 | 0.274 | 0.276 | 0.28 |
| 400 | 0.135 | 0.134 | 0.137 | 0.128 | 0.133 | 0.134 |

Table 3.7 indicates the change in absorbance (i.e., % absorbance retained) for samples stored in the dark for approximately the same amount of time as irradiation (Tables 3.1-3.3).

| Wavelength (nm) | Formulation #1 |
|---|---|
| 290 | 98.4 |
| 295 | 98.6 |
| 300 | 98.4 |
| 305 | 97.9 |
| 310 | 98.7 |
| 315 | 98.6 |
| 320 | 98.2 |
| 325 | 97.9 |
| 330 | 98.5 |
| 335 | 98.1 |
| 340 | 97.8 |
| 345 | 98.1 |
| 350 | 98.2 |
| 355 | 97.9 |
| 360 | 98.0 |
| 365 | 98.0 |
| 370 | 98.0 |
| 375 | 97.9 |
| 380 | 97.7 |
| 385 | 97.2 |
| 390 | 96.4 |
| 395 | 96.2 |
| 400 | 97.3 |

Table 3.8 (below) shows the average percent absorption retained after irradiation and after corrections based on the dark stored samples.

| Wavelength (nm) | Corrected % Formulation #1 |
|---|---|
| 290 | 90.5 |
| 295 | 90.1 |
| 300 | 90.2 |
| 305 | 90.4 |
| 310 | 88.7 |
| 315 | 89.0 |
| 320 | 89.5 |
| 325 | 89.8 |
| 330 | 90.6 |
| 335 | 91.3 |
| 340 | 91.4 |
| 345 | 90.8 |
| 350 | 90.6 |
| 355 | 90.7 |
| 360 | 90.4 |
| 365 | 90.2 |
| 370 | 90.4 |
| 375 | 90.5 |
| 380 | 90.5 |
| 385 | 91.0 |
| 390 | 92.9 |
| 395 | 96.1 |
| 400 | 104.5 |

Table 3.9 (below) SPF, UVA/UVB ratio, and Critical wavelength prior to and after irradiation with a solar simulator*

| Sample # | SPF Initial | SPF Post Irradiation | UVA/UVB Ratio-Initial | UVA/UVB ratio - Post Irradiation | CW Initial | CW Post Irradiation |
|---|---|---|---|---|---|---|
| 10-021-1 | 39.9 | 26.74 | .73 | .735 | 378.5 | 378.5 |
| 10-021-2 | 52.48 | 31.5 | .744 | .75 | 378.6 | 378.7 |
| 10-021-3 | 61.83 | 42.58 | .739 | .741 | 378.5 | 378.5 |
| 10-021-19 | 53.3 | 40.37 | .694 | .693 | 378.6 | 378.5 |
| 10-021-20 | 66.83 | 47.98 | .699 | .702 | 378.5 | 378.5 |
| 10-021-21 | 76.05 | 57.63 | .703 | .703 | 378.6 | 378.6 |
| 10-021-25 | 65.86 | 48.01 | .694 | .685 | 377.9 | 378.1 |
| 10-021-26 | 54.26 | 38.22 | .693 | .681 | 377.9 | 378.1 |
| 10-021-27 | 80.15 | 60.04 | .705 | .689 | 378 | 378.2 |

CW = Critical wavelength
*Values not corrected (i.e., based on dark sample).

What is claimed is:

1. A photostable sunscreen composition consisting essentially of:
   (a) as the sole organic sunscreen that absorbs ultraviolet radiation from 310-400 nm butylmethoxydibenzoylmethane, at a concentration of from 2.7 to 3.3 wt-%, and
   (b) a four-component photostabilizing complex that quenches singlet-excited energy and/or triplet-excited energy of butylmethoxy-dibenzoylmethane after exposure to ultraviolet radiation, said complex consisting of
      (i) 2.5 to 3.1 wt-% octocrylene,
      (ii) 5.4 to 6.6 wt-% oxybenzone,
      (iii) 0.1 to 1.0 wt-% Polysilicone-15, and
      (iv) 0.001 to 0.5 wt-% of an extract of *Haematococcus pluvialis*,
wherein the photostable sunscreen composition retains 85% of its UV absorbance over the range of 290 nm to 400 nm after being irradiated with 15 MEDs of energy from a simulated solar radiation source calibrated in accordance with the COLIPA standard.

2. The photostable sunscreen composition of claim 1 wherein the photostable sunscreen retains 90% of its UV absorbance over the range of 290 nm to 400 nm after being irradiated with 15 MEDs of energy from a simulated solar radiation source calibrated in accordance with the COLIPA standard.

3. The photostable sunscreen composition of claim 1 wherein the ratio of Polysilicone-15 to butylmethoxydibenzoylmethane, by weight, is about 1:3.

4. The photostable sunscreen composition of claim 1 wherein the ratio of butylmethoxydibenzoylmethane:octocrylene:oxybenzone is between about 1:0.9:2 and 1.1:1:2.2.

5. The photostable sunscreen formulation of claim 1 further consisting essentially of two esters of salicylic acid in a total amount of 4.5 wt-% to 16.5 wt-% wherein at the time of initial application the SPF of the photostable sunscreen composition is at least 55.

6. The photostable sunscreen composition of claim 5 wherein the esters of salicylic acid are octisalate and homosalate.

7. The photostable sunscreen composition of claim 6 wherein the total amount of esters of salicylic acid, by weight, is between 13.5 wt-% and 16.5 wt-%.

\* \* \* \* \*